United States Patent [19]

Dazey et al.

[11] Patent Number: 5,760,183

[45] Date of Patent: Jun. 2, 1998

[54] PROCESS FOR THE MANUFACTURE OF VERY HIGH-PURITY ANTITHAEMOPHILIC FACTOR (FVIIIC), AND VON WILLEBRAND FACTOR, AND PHARMACEUTICAL COMPOSITIONS CONTAINING SAME

[75] Inventors: Bernard Dazey; Mohamed Hamsany, both of Bordeaux; Gérard Vezon, Cursan, all of France

[73] Assignee: Association d'Aquitaine pour de Developpment de la Transfusion Sanguine et des Recherches Hematologiques, France

[21] Appl. No.: 16,807

[22] Filed: Feb. 11, 1993

Related U.S. Application Data

[63] Continuation-in-part of Ser. No. 476,978, Feb. 7, 1990, abandoned, and Ser. No. 739,452, Aug. 2, 1991, Pat. No. 5,252,710.

[30] Foreign Application Priority Data

Feb. 17, 1989 [FR] France ................................ 89 02136
Aug. 2, 1990 [FR] France ................................ 90 09917

[51] Int. Cl.$^6$ ......................... C07K 1/18; C07K 14/745; C07K 14/755
[52] U.S. Cl. ............................................. 530/383; 530/416
[58] Field of Search ........................... 530/380, 383, 530/384, 412, 416

[56] References Cited

U.S. PATENT DOCUMENTS

| | | | |
|---|---|---|---|
| 4,170,590 | 10/1979 | Stephan et al. | 530/383 |
| 4,278,594 | 7/1981 | Amrani | 530/381 |
| 4,670,543 | 6/1987 | Bourgois et al. | 514/8 |
| 4,774,323 | 9/1988 | Newman et al. | 530/383 |
| 4,883,598 | 11/1989 | Reithorst et al. | 530/381 |
| 5,252,709 | 10/1993 | Burnouf et al. | 530/383 |
| 5,259,951 | 11/1993 | Arrighi et al. | 530/383 |

FOREIGN PATENT DOCUMENTS

| | | | |
|---|---|---|---|
| 383645 | 8/1990 | European Pat. Off. | |
| 469985 | 2/1992 | European Pat. Off. | 530/383 |
| 2650393 | 2/1991 | France | 530/383 |

OTHER PUBLICATIONS

J. Lab. Clin. Med., vol. 89, No. 6, issued Jun. 1977, Olson et al, "Purification of Porcine and Human ristocetin–Willebrand factor", pp. 1278–1294.

DBA Abstract, PCT WO 89–12065, Dec. 14, 1989.

British Journal of Haematology, vol.43, issued 1979, Austen, "The Chromatographic Separation of Factor VIII . . . ", pp. 669–674.

Primary Examiner—Jeffrey E. Russel
Attorney, Agent, or Firm—Londa and Traub LLP

[57] ABSTRACT

The invention relates to a process for the manufacture of very high-purity antihemophilic factor (FVIIIc) and von Willebrand factor. This process enables the manufacture of very high-purity antihemophilic factor (FIIIc) devoid of the bulk of the Willebrand factor comprises a step for purification by ion exchange chromatography with the aid of a chromatography column containing a gel, the purification step comprising a step for adsorption of the antihemophilic factor essentially devoid of the Willebrand factor on the gel in the column and a step for desorption of the purified antihemophilic factor, which is collected, thereby obtaining an antihemophilic factor devoid of the bulk of the Willebrand factor and having an activity as high as 250 IU/mg of proteins. This process also permits to recover von Willebrand factor in very high purity.

26 Claims, No Drawings

PROCESS FOR THE MANUFACTURE OF VERY HIGH-PURITY ANTITHAEMOPHILIC FACTOR (FVIIIC), AND VON WILLEBRAND FACTOR, AND PHARMACEUTICAL COMPOSITIONS CONTAINING SAME

This application is a Continuation-in-Part of applications Ser. No. 07/476,978 of Feb. 7, 1990 which is now abandoned in favor of the present application and Ser. No. 739,452 of Aug. 2, 1991 for which the claims have been allowed and the issue fee was paid on Jun. 22, 1993, now U.S. Pat. No. 5,252,710.

The invention relates essentially to a process for the manufacture of very high-purity Antihaemophilic Factor FVIIIc, and von Willebrand Factor, and to a pharmaceutical composition containing same.

STATE OF THE ART

Various processes for the purification of Antihaemophilic Factor (FVIIc) are already known in the prior art. For example, patent document WO 86/04486 (New York University) describes a method of purifying Antihaemophilic Factor using column chromatography techniques in the presence of sugar, polyhydric alcohol, amino acid or salt (see page 1, lines 16 to 23, and claim 1, page 30).

In this process of the prior art, these additives, including sugars, polyhydric alcohols, amino acids or salts, are added at any stage of the process, i.e. before the chromatography, during the chromatography or at the end of the chromatography.

It should be noted that this addition of sugar was widely used in the prior art, since numerous articles relating to the purification of Factor VIIc by chromatography are cited on pages 3 and 4 of the text of this very document. Reference may usefully be made in this connection to the document by Austen in Thronib. Haemostas. (Stuttgart) 48 (1):46 (1982), which describes a process for the treatment of plasma by chromatography on a column of aminohexyl Sepharose with the aid of a buffered wash solution of lysine acetate and a saline gradient for eluting the column. Similarly, in J. Chromatog. 257:387 (1983), Faure describes the use of 1 and 10 % of sucrose in lysine acetate buffers for improving the yield of Factor VIIIc during the chromatography of a cryoprecipitate on an aminohexyl Sepharose gel used in the chromatography column. The authors indicate that the use of sugar makes it possible to inhibit the formation of a molecular complex. Said document corresponds to patent document U.S. Pat. No. 4,743,680.

Examples of other prior art documents are U.S. Pat. No. 4,508,709=EP-A-144 957 or U.S. Pat. No. 4,578,218=DE-A-3 504 385. Another process of the prior art is described in patent document FR-A-2-570 276; this leads to the presence of immunoglobulins of murine origin, having some disadvantages in human therapy which are readily understandable to those skilled in the art.

In particular, patent document EP-A-144 957 to ARMOUR (also=U.S. Pat. No. 4,508,709) describes a process for the purification of Factor VIIc which is based on a combined adsorption of Factor VIIIc and Willebrand Factor, followed by a selective desorption of Factor VIIIc and Willebrand Factor in order to eliminate the Willebrand Factor. This procedure is fundamentally different from the process of the invention, the aim of which, as will be seen below, is principally to adsorb only Factor VIIIc, essentially without Willebrand Factor. Moreover, for adsorption of the Factor VIIIc/Willebrand Factor mixture, ARMOUR uses an eluting solution, called "buffer A" at a pH of about 6.8, which does not contain $CaCl_2$ (see page 5, lines 6 to 18, and page 6, lines 14 to 26).

ARMOUR then carries out washings with modified buffer solutions containing 10 millimol of $CaCl_2$. ARMOUR emphasizes that $CaCl_2$ is known in the art for stabilizing Factor VIIIc, but cannot be used in the prior art because of the danger of activating the clotting factors, leading to fibrin clots on the resin and potential degradation of the factor VIIc (see page 6, line 27, to page 7, line 5).

Thus there was a prejudice in the art against the use of initial eluting solutions containing $CaCl_2$.

SUMMARY OF THE INVENTION

Now, as will be seen below, the present invention opposes this prejudice in the art by aiming for selective adsorption of Factor VIIIc essentially devoid of Willebrand Factor and by using for this purpose a first eluting solution which contains $CaCl_2$ in an amount of 10 millimoles.

On the other hand, the invention provides a process which permits to yield a very high-purity in von Willebrand Factor.

One object of the present invention is therefore to solve the novel technical problem consisting in the provision of a process for the manufacture of very high-purity Antihaemophilic Factor (FVIIIc) without murine immunoglobulins, which does not contain contaminants capable of causing trouble for the haemophilic patient.

A further object of the present invention is to solve the novel technical problem consisting in the provision of a process forc the manufacture of Antihaemophilic Factor (FVIIIc) isolated from the bulk of the Willebrand Factor, in contrast to certain techniques of the prior art and especially that described in patent document FR-A-2 570 276 or EP-A-144 957 (=U.S. Pat. No. 4,508,709), thus making it possible to significantly increase the activity of the resulting Antihaemophilic Factor up to values as high as 250 international units (IU) per mg of proteins.

A further object of the present invention is to provide a von Willebrand Factor of very high-purity, by a simple manufacturing process enabling good reproducibility to be obtained as well as very large quantities to be processed on an industrial scale, while being relatively inexpensive.

A further object of the present invention is to solve these novel technical problems by means of a particularly simple and reproducible manufacturing process which can be used on the industrial scale.

The present invention provides for the first time a satisfactory solution to these technical problems which is such that it can be used on the industrial scale by making it possible to treat large amounts with no volume limitation, this being in contrast to the techniques of the prior art, which were restricted to the laboratory.

Moreover, the invention effects viral inactivation, for which there is no provision in the prior art documents.

Thus, according to a first feature, the present invention provides a process for the manufacture of very high-purity Antihaemophilic Factor (FVIIIc) devoid of the bulk of the Willebrand Factor comprising providing a first ion exchange chromatography column containing a first ion exchange gel; preparing a first buffered eluting solution which has an ionic strength capable of separating Factor VIIIc from the bulk of the Willebrand Factor and its main plasma contaminants, a crude solution containing both Factor VIIIc and Willebrand Factor is prepared from a cryoprecipitate, said crude solution having a substantially identical ionic strength to that of the first buffered eluting solution, by eluting said crude solution with said first eluting solution thereby selectively adsorbing the Factor VIIIc essentially devoid of Willebrand Factor on the first gel in the first column whereas the non-retained fraction contains the von Willebrand Factor largely devoid of factor VIIIc which may be treated later for the purpose of obtaining it in purified form, and desorbing the Factor VIIIc adsorbed on the first gel in the first column by means of the first eluting solution by using a second buffered eluting solution of higher ionic strength than the first eluting solution, thus giving a purified solution of Factor VIIIc of very high purity which is devoid of the bulk of the Willebrand Factor and the main plasma contaminants.

In an advantageous variant of the process according to the invention, diafiltration is then carried out against a third buffer solution, preferably permitting intravenous injection. According to another advantageous characteristic, the purified solution of Factor VIIIc is concentrated and preferably also lyophilized.

In a variant of the process according to the invention, the crude solution of Factor VIIIc to be purified is prepared by dissolving a cryoprecipitate extracted from human plasma.

According to another advantageous characteristic of the process according to the invention, the solution obtained by dissolving the cryoprecipitate in water to which heparin has advantageously been added is treated with aluminum hydroxide. The proportion in which aluminum hydroxide is incorporated is not critical and can vary within wide limits. It is preferred, however, to use a proportion greater than 10% by volume, relative to the total volume of the solution containing Factor VIIIc. Currently preferred proportions are of the order of 15% by volume.

Advantageously, centrifugation is then carried out in order to separate the aluminum hydroxide from the solution of Factor VIIIc, from which the vitamin K dependent factors are thereby removed. In an advantageous variant of the process according to the invention, the solution containing Factor VIIIc can then be virally inactivated with the aid of a buffer solution containing a solvent/detergent mixture, as described in patent document EP-A-0 131 740 or U.S. Pat. No. 4,540,573.

The crude solution of Factor VIIIc to be purified is preferably subjected to diafiltration against the first buffer solution used to elute the column, before passing on to the adsorption step on the column.

According to one advantageous characteristic of the process according to the invention, the purification gel used in the ion exchange chromatography column is a gel having the following essential characteristics:

- an ion exchange gel of the anionic type based on agarose crosslinked in particular to the extent of about 6%, in the form of beads. This gel is preferably of the quaternary amine type, especially at the end of a short spacer arm, for example of the $C_1$–$C_6$ alkylene type, linked to the agarose beads.
- a gel which corresponds to these characteristics and which is commercially available is known under the tradename Q-Sepharose fast flow® and marketed by the Swedish company Pharmiacia, the beads having a diameter of 45–165 μm in the wet state.

According to another advantageous characteristic of the process according to the invention, the first buffered eluting solution has the following composition:

NaCl 250 mM

Tris 20 mM $CaCl_2.2H_2O$ 10 mM

This composition is brought to pH 6.6 by adding concentrated acid. The acid is preferably concentrated HCl and notably concentrated HCl 12N.

According to another advantageous characteristic of the process according to the invention, the second buffer solution, used for desorption of the Factor VIIIc from the column, has the following composition:

NaCl 700 mM

Tris 20 mM $CaCl_2.2H_2O$ 10 mM

This composition is also brought to pH 6.6 with said concentrated acid.

According to yet another advantageous characteristic of the process according to the invention, the third buffer solution mentioned above, used for diafiltration of the purified and eluted Factor VIIIc, has the following conditioning composition:

NaCl 100 mM

Tris 20 mM $CaCl_2.2H_2O$ 0.6 mM

L-arginine 17 mM

L-lysine-HCl 20 mM

This solution is also brought to pH 7 with said concentrated acid.

According to an advantageous characteristic of the process according to the invention, before this diafiltration is carried out with the third buffer solution, 17 mM of L-arginine and 20 mM of L-lysine-HCl per liter of solution are added to the purified and eluted solution of Factor VIIIc.

According to an advantageous characteristic of the process of the invention, the above-mentioned diafiltrations are performed with diafiltration membranes treated with a 0.1M bicarbonate buffer at pH 9.6, containing 30 g/l of non-pyrogenic human albumin and 0.1% by volume of emulsifier.

To preserve the very high-purity eluted solution of Factor VIIIc obtained in this way, which is devoid of the bulk of the Willebrand Factor and has an antihaemophilic activity A of at least 250 IU/mg of proteins, it is subjected to sterilizing filtration on a sterilizing filter with a pore diameter of 0.22 μm, and this purified and sterilized solution of Factor VIIIc is then introduced into silicone-treated flasks.

According to a second feature, the present invention also provides very high-purity Factor VIIIc which has been obtained by the process described above. The invention also covers very high-purity Factor VIIIc which is devoid of the bulk of the Willebrand Factor. Preferably, the antihaemophilic activity A of the Factor VIIIc according to the invention is at least 250 IU/mg of proteins.

According to a third feature, the present invention also covers a pharmaceutical composition which contains Factors VIIIc as obtained by the process according to the invention or as defined above. Preferably, this therapeutic composition contains the Factor VIIIc in lyophilized form, with which an injectable preparation can be made up for immediate use.

According to a fourth aspect, the present invention provides a process for manufacturing von Willebrand Factor having a very high-purity, largely devoid of antihaemophilic factor (FVIIIc), comprising a step of purification by ion exchange chromatography using a first chromatography column containing a first gel, comprising a step of adsorption of only the antihaemophilic factor on the first gel of the said first column, which factor will be desorbed later for the purpose of obtaining it in purified form, while the von Willebrand Factor largely devoid of Factor VIIIc is contained in the non-retained fraction and is then treated in order to obtain it in a purified form, the non-retained fraction containing the von Willebrand Factor is treated so as to decrease the ionic strength of the non-retained solution until an ionic strength corresponding to that which is obtained with a 0.1 to 0.15M NaCl solution is obtained, and the vonWillebrand Factor is then adsorbed selectively on a second ion exchange gel of a second ion exchange chromatography column, eluting the said non-retained solution of reduced ionic strength with a fourth elution which has an ionic strength substantially identical to that of the non-retained solution having reduced ionic strength; the von Willebrand Factor adsorbed on the second gel of the second column is then desorbed by means of a fourth elution solution of higher ionic strength than the fourth elution solution, and collecting said von Willebrand Factor desorbed with said second elution solution, thereby yielding a purified solution of von Willebrand Factor of very high-purity, largely devoid of antihaemophilic Factor VIIIc and of inactivators such as Tween and TNBP, as well as of the main plasma contaminants.

According to an advantageous embodiment of the process according to this fourth aspect, the ionic strength of the non-retained solution is reduced by carrying out a diafiltration, preferably preceded by a concentration. This diafiltration is advantageously carried out against a fourth buffer solution, which is identical to that used for equilibrating and eluting the second column to selectively adsorb the von Willebrand factor (see hercbelow). Such a fourth buffer solution for the diafiltration advantageously has the following composition:

NaCl 100–150 mM

Tris 20 mM

This solution is also brought to pH 6.6, with concentrated acid, in particular HCl 12N.

According to a particular feature of the invention, the concentration of the diafiltered solution is carried out so as to obtain between 30 and 40 units of von Willebrand Factor:RCO (ristocetin cofactor).

According to a preferred variant of embodiment of the process according to this fourth aspect, the fourth elution solution which enables the von Willebrand Factor to be adsorbed selectively on the second gel of the second column has the following composition:

NaCl 100–150 mM

Tris 20 mM

This solution is brought to pH 6.6 with concentrated acid, in particular HCl 12N.

According to another particular feature of the process according to the invention, an eluting solution of the following composition:

NaCl 350 mM

Tris 20 mM is used as a fifth elution solution which enables the von Willebrand Factor to be desorbed from the second column. This composition is brought to pH 6.6 with said concentrated acid, in particular HCl 12N.

According to another advantageous feature of the process according to the invention, the purification gel which is used in the second ion exchange chromatography column, for selectively adsorbing the von Willebrand Factor, is a gel having the following essential features:

a gel for exchanging anionic type ions, based on crosslinked agarose, especially having a concentration of approximately 6%, in bead form. This gel is preferably of the type possessing quaternary amino groups, in particular at the end of a small spacer arm, for example of the $C_1$–$C_6$ alkylene type, linked to the agarose beads.

A gel which corresponds to these features and which is commercially available is known under the trade name Q Sepharose fast flow® and marketed by the Swedish company Pharmacia, the beads of which have a diameter of 45–165 μm in the wet state.

It should be noted that this gel surprisingly displays a good affinity with respect to von Willebrand Factor, of the order of 50 units of von Willebrand Factor: Rag per liter of gel.

According to a particular feature of the process according to the invention, a cryoprecipitate extracted from human plasma, which is dissolved, preferably by dissolution in water, advantageously with the addition of heparin, is used as a source of von Willebrand Factor. The solution thereby obtained is treated with aluminium hydroxide. The proportion in incorporation of aluminium hydroxide is not critical and can vary within wide limits. It is preferable, however, to use a proportion greater than 10% by volume relative to the total volume of the starting solution. Currently preferred proportions are of the order of 15% by volume.

Advantageously, a centrifugation is also carried out to separate the aluminium hydroxide from the starting solution, in order to free the latter from vitamin K-dependent factors. However, according to an advantageous variant of embodiment of the process according to the invention, the solution initially containing Factor VIIIc as well as the von Willebrand Factor can then be inactived virally using a buffer solution containing a solvent/detergent mixture as described in the document EP-A-0, 131, 740 or U.S. Pat. No. 4,540, 573.

The virally inactived, crude solution thereby obtained is freed from Factor VIIIc according to the method described in the previous document of the Application FR 89/02,136, which is incorporated herein by reference.

It will simply be noted that, before proceeding to a step of adsorption on a first ion exchange chromatography column containing a Factor VIIIc-binding gel, a diafiltration of the crude solution is carried out using a buffer solution identical to that used for elution of the first column used for binding the Factor VIIIc.

Accordingly the invention provides both the selective adsorption of the Factor VIIIc carried out on a first column, while the von Willebrand Factor is present in the non-retained eluted solution which may then be treated to be purified in a second column.

Thus the invention provides a unique process for yielding high-purified Factor VIIIc and von Willebrand Factor independently or simultaneously. Further it is remarkable that the same ion exchange gel can be used for both selective separation of Factor VIIIc and von Willebrand Factor which simplifies the process and greatly lowers the costs.

As regards the preferred step of diafiltration of the non-retained eluted solution containing the von Willebrand factor, a membrane having a cut-off capability at 100.000, for example a Millipore reference 4PTHK type membrane of the company Millipore, is used.

Moreover, for the purpose of preservation of the eluted solution of von Willebrand Factor of very high-purity obtained by the process according to the invention, largely devoid of antihaemophilic Factor VIIIc and displaying a specific activity of more than 50 in terms of von Willebrand Factor:RCO per mg of protein, a sterilising filtration is carried out on a sterilising filter having a pore size of diameter 0.22 μm, and this sterilised, purified solution of von Willebrand Factor is then introduced into conventional vials.

A last diafiltration against a sixth condionning buffer solution identical to the third conditioning buffer solution above described can be performed.

In a fifth aspect, the present invention also provides von Willebrand Factor of very high-purity, characterised in that it has been obtained by the process described above. The invention also covers von Willebranid Factor of very high-purity, characterised in that it is largely devoid of Factor VIIIc, preferably having a Factor VIIIc content of less than 2%. Preferably, the specific activity of the von Willebrand Factor according to the invention is at least 50 von Willebrand: RCO units/mg of protein.

According to a sixth aspect, the present invention also covers a pharmaceutical composition, characterised in that it contains von Willebrand Factor as obtained by the process according to the invention or as defined above. Preferably, this pharmaceutical composition contains von Willebrand Factor in lyophilised form, which enables an injectable preparation to be prepared at the time of use.

The invention also covers a process for manufacturing a pharmaceutical composition, characterised in that von Willebrand Factor largely devoid of Factor VIIIc, advantageously having a Factor VIIIc content of less than 2%, is used as active principle. Preferably, this von Willebrand Factor is in lyophilised form, which ajoins the Factor VIIIc method and enables an injectable preparation to be prepared at the time of use.

Again, the invention covers a method for the treatment of mammals, including humans, suffering from Factor VIIIc's disease, characterised in that a therapeutically effective amount of Factor VIIIc which is largely devoid of von Willebrand, having an advantageous von Willebrand Factor content of less than 2%, is administered to these mammals, including humans.

Lastly, the invention covers a method for the treatment of mammals, including humans, suffering from von Willebrand's disease, characterised in that a therapeutically effective amount of von Willebrand Factor largely devoid of Factor VIIIc, advantageously having a factor VIIIc content of less than 2%, is administered to the said mammals, including humans. According to a particular embodiment, the specific activity of the von Willebrand Factor is at least 50 von Willebrand: RCO units/mg of protein. This von Willebrand Factor is, according to a particular variant of embodiment, in the form of a preparation for parenteral injection, prepared at the time of use from a lyophilised form. With the von Willebrand Factor obtained according to the present invention, the administration dose will customarily be from 30 to 40 units of vW:RCO/kg of body weight/day.

DETAILED DESCRIPTION OF THE INVENTION

Further objects, characteristics and advantages of the invention will become clear from the following explanatory description referring to two examples of the best embodiments given simply by way of illustration and which cannot thereof in any way limit the scope of the invention. In these examples, the percentages are given by weight, unless indicated otherwise.

EXAMPLE 1 OF THE INVENTION

Selective purification of Factor VIIIc 3 kg of cryoprecipitate of human blood plasma, originating from 300 l of human plasma, are dissolved in 3.2 times its volume of Limulus-negative osmosed aqueous solution to which heparin has been added at a concentration of 3 IU/ml of solution, at laboratory temperature for 2 h, with stirring, so as to effect complete dissolution.

After measurement of the final volume, aluminium hydroxide is added to this solution at a rate of 15% by volume, relative to the total volume of this solution, in order to eliminate the vitamin K dependent factors. The mixture is stirred for 5 min in order to effect this adsorption of the vitamin K dependent factors on the aluminium hydroxide.

The aluminium hydroxide is separated from the solution by centrifugation at 6000 G.

The solution containing Factor VIIIc is then treated according to the process described in patent document U.S. Pat. 4,540,573 so as to effect viral inactivation.

The solution containing the inactivated Factor VIIIc is then subjected to diafiltration against a first buffer solution, which will subsequently be used for equilibration and first elution of the chromatography column, said buffer solution having the following composition:

NaCl 250 mM

Tris 20 mM $CaCl_2.2H_2O$ 10 mM

This solution was brought to pH 6.6. with 12N concentrated HCl.

This diafiltration is performed with twice the volume of the inactivated solution of Factor VIIIc, thus eliminating the bulk of the products used for viral inactivation. This first membrane used for diafiltration is a Millipore membrane, reference 4PFHK, with a cut-off threshold of 100,000. This procedure gives an inactivated solution of Factor VIIIc which has been subjected to dialfiltration and concentrated to 10 L total solution.

A check is made to ensure that this solution concentrated to 10 L has substantially the same ionic strength as the first buffer solution for eluting the chromatography column. The chromatography column is, for example, a column of 25 cm in height and 40 cm in diameter, into which 32 L of Q-Sepharose fast flow® gel from Pharmacia are introduced.

The gel was equilibrated with the first eluting solution before the 10 L of solution of Factor VIIIc to be purified were injected at a rate of 25 L per hour, this being followed by injection, at the same rate, of the first buffered eluting solution until protein peaks are no longer observed at the column outlet, as verified with a spectrophotometer at 280 nm, said peaks corresponding mainly to Willebrand Factor, fibrinogen, albumin and α-globulins which it is desired to eliminate.

After this elution of the column with the first buffered eluting solution, a second buffered eluting solution of higher ionic strength and having the following composition:

NaCl 700 mM

Tris 20 mM $CaCl_2.2H_2O$ 10 mM which has been brought to pH 6.6 by the addition of 12N concentrated HCl, is used as the eluting solution.

This elution with the second buffer solution is carried out, at the same rate as before, until the peak corresponding to Factor VIIIc is observed. This observation is made by modifying the sensitivity of the spectrophotometer in a manner which is very evident to those skilled in the art.

It will be observed that, in the unretained initial peak which contained especially all the contaminants, including Willebrand Factor, a volume of 80 to 100 L of solution is recovered; this is set aside and may be treated for separation of the Willebrand Factor in purified form, which has a therapeutic value well known to those skilled in the art in connection with Willebrand's disease.

Furthermore, the solution of Factor VIIIc obtained after elution has a total volume of 40 to 50 l, in which Factor VIIIc is present in a very small proportion, i.e. between 0.5 and 1 IU/ml.

17 mMol of L-arginine per liter of solution and 20 mMol of L-lysine-HCl per liter of solution are added to the diluted solution to provide the following composition (named third conditioning buffer solution):

NaCl 100 mM
Tris 20 mM
$CaCl_2.2H_2O$ 0.6 mM
L-arginine 17 mM
L-lysine HCl 20 mM this solution having been brought to a pH of 7 with 12N concentrated HCl.

This procedure makes it possible to reduce the proportion of sodium to 100 mM per liter of solution and concentrate Factor VIIIc to 30 IU/ml. The diafiltration membrane used in this step is a Millipore membrane, reference 4PITK, with a cut-off threshold of 30,000.

It should be noted that it is very important to pretreat all the diafiltration membranes by rinsing them copiously with Limulus-negative osmosed water. In a separate operation, 5 L of 0.1M bicarbonate buffer at pH 9.6, containing 30 g/l of non-pyrogenic human albumin and 0.1% by volume of an emulsifier, for example Tween 80®, were prepared and injected through these membranes by means of an ASTI® pump with a Teflon piston and a Pyrex body, for 2 h in closed circuit. The membranes are then rinsed for 1 h with Limulus-negative osmosed water, after which 20 L of the second buffer solution mentioned above are passed through. A check is made to ensure that the level of protein at the outlet of the diafiltration membrane is zero by means of a protein assay using the micromethod of Marion M. Bradford described in ANALYTICAL BIOCHEMISTRY 72, 248–254 (1976).

Sterilizing filtration of the solution of Factor VIIIc is then carried out on a sterilizing membrane, for example the one from Millipore, reference Millidisk, with a pore diameter of 0.22 µm.

This gives a sterilized, very divided up solution of Factor VIIIc which can be divided up into silicone-treated flasks for product storage, especially for the purpose of lyophilization, which can then be carried out in completely conventional manner. This procedure gives a Factor VIIIc of 30 IU/ml with a specific activity of at least 250 IU/mg of protein.

This Factor VIIIc, which is advantageously to be lyophilized, thus constitutes a pharmaceutical composition of very great value which makes it possible for the patient suffering from haemophilia to be injected only with the amounts of product necessary for treating his haemophilia; this represents a decisive technical advance which is totally unexpected by those skilled in the art.

It should also be observed that this product has a very high stability with time. In particular, the activity of the Factor VIIIc drops by less than 10% after the lyophilizate has been taken up 24 h later.

Moreover, the process according to the invention makes it possible to obtain excellent yields on the industrial scale, which are of the order of 50 to 55% relative to the initial dissolved cryoprecipitate.

EXAMPLE 2 OF THE INVENTION

Selective purification of von Willebrand Factor 3 kg of cryoprecipitate of human blood plasma, derived from 300 l of human plasma, are dissolved in 3.2 times its volume of solution of limulus-negative, osmotically purified water to which heparin was added in the proportion of 3 international units per ml of solution, at laboratory temperature and with stirring for 2 h so as to produce complete dissolution.

After measurement of the final volume, aluminiumn hydroxide is added to this solution in the proportion of 15% by volume relative to the total volume of this solution in order to remove vitamn K-dependent factors. The mixture is left stirring for 5 min in order to achieve this adsorption of the vitamin K-dependent factors on the aluminium hydroxide.

The mixture is centrifuged at 6,000 g in order to separate the aluminium hydroxide from the solution.

The crude solution containing factor VIIIc as well as the desired von Willebrand Factor is treated according to the process described in the document U.S. Pat. No. 4,540,573 so as to produce a viral inactivation.

A diafiltration of the crude solution containing Factor VIIIc as well as von Willebrand Factor is then carried out against a first buffer solution which will then be used for equilibration and elution of the first chromatography column used for selectively adsorbing Factor VIIIc, having the following composition:

NaCl 250 mM
Tris 20 mM
$CaCl_2.2H_2O$ 10 mM

This solution has been brought to pH 6.6 with 12N concentrated HCl.

This diafiltration is carried out with twice the volume of the crude solution containing Factor VIIIc as well as von Willebrand Factor, the solution being inactivated by thereby removing most of the products which were used for the viral inactivation. The membrane used for the diafiltration is a Millipore reference 4PTwHK membrane having a cut-off capability at 100,000. A crude solution containing Factor VIIIc as well as von Willebrand Factor is thereby obtained, the solution being inactivated, diafiltered and concentrated to 10 L of total solution.

It is checked that this solution concentrated to 10 L has substantially the same ionic strength as the elution buffer solution of the first chromatography column used for selectively adsorbing Factor VIIIc. The chromatography column is, for example, a column 25 cm high by 40 cm in diameter into which 32 L of the company Pharmacia's Q Sepharose fast flow® gel are introduced (first gel).

The first gel has been equilibrated with the elution solution before carrying out the injection of the 10 L of crude solution containing Factor VIIIc and von Willebrand Factor, at the rate of 25 L/h for an injection of the elution buffer solution at the same flow rate until a protein peak is no longer observed in the outflow from the column, by checking with a spectrophotometer at 280 nm, this peak corresponding mainly to the von Willebrand Factor, fibrigen, albumin and γ-globulins as well as plasma inactivators which it is desired to collect separately for the purpose of recovering the von Willebrand Factor.

After elution of the first column with the elution buffer solution, the Factor VIIIc has thereby been adsorbed selectively on this column. Moreover, the non-retained eluted solution contains the von Willebrand Factor, fibrinogen, albumin and γ-globulins as well as the plasma inactivators, and has a volume of 80 to 100 liters.

The von Willebrand factor is separated selectively by the process according to the invention in the following manner:

In the first place, a diafiltration of the non-retained eluted solution containing the von Willebrand Factor is carried out against a fourth buffer solution of the following composition which is the same as that used for equilibrating and eluting the second column:

NaCl between 100 and 150 mM, preferably approximately 120 mM
Tris 20 mM

This solution is brought to a pH equal to 6.6 with 12N concentrated HCl.

This solution is diafiltered with Millipore reference 4PTHK membrane having a cut-off capability at 100,000 under conditions producing a simultaneous concentration until a volume of 10 L of total solution is obtained.

It is checked that this solution of von Willebrand Factor concentrated to 10 L has substantially the same ionic strength as the fourth elution buffer solution of the second chromatography column used for the selective adsorption of the von Willebrand Factor.

The selective adsorption of the von Willebrand Factor is, then carried out on this second chromatography volume containing the same gel as the first chromatography column used for the selective adsorption of Factor VIIIc, but which has been equilibrated here to an ionic strength corresponding to that of the von Willebrand solution, which is between 100 and 150 mM with respect to NaCl. Thus the fourth eluting solution enabling the von Willebrand Factor to be adsorbed selectively on the second gel of the second column has the following composition:

NaCl between 100 and 150 mM, preferably approximately 120 mM
Tris 20 mM

This solution has been brought to pH 6.6 in particular with concentrated acid.

The eluted and unbound portion emerging from this second column essentially contains fibrinogen, fibronectin, albumin and γ-globulins as well as plasma inactivators, which are set on one side.

Moreover, the von Willebrand Factor adsorbed on the column is collected by elution with a fifth elution solution having a higher ionic strength, of the following composition:

NaCl between 300 and 350 mM, preferably approximately 350 mM
Tris 20 mM

This solution has been brought to pH 6.6 with 12N concentrated HCl.

In this second chromatography column, specific for the binding of von Willebrand Factor, it suffices to use 8 L of Pharmacia Q Sepharose fast flow® gel on account of the much higher affinity of this gel with respect to von Willebrand Factor.

This eluted solution containing the purified von Willerand factor is now concentrated by diafiltering it against a sixth conditioning buffer solution having the following composition:

NaCl approximatively 100 mM
Tris 20 mM
$CaCl_2.2H_2O$ 0.6 mM
L-arginine 17 mM
L-lysine HCl 20 mM This approach makes it possible to decrease the proportion of sodium to 100 mM/l and to concentrate between 30 and 40 international units of von Willebrand Factor:RCO per ml of solution. The diafiltration membrane which is used in this step is a Millipore reference 4PTHK membrane having a cut-off capability at 100.00.

A sterilising filtration of the solution of von Willebrand Factor is then carried out on a sterilising membrane, for example that of the company Millipore reference Millidisk having a pore diameter of 0.22 μm.

A sterilised solution of von Willebrand Factor of very high-purity is thereby obtained, which solution may be distributed in vials for storage of the products, in particular for the purpose of lyophilisation which may then be carried out in an altogether conventional manner. A von Willebrand factor having a specific activity of at least 50 von Willebrand:RCO units/mg of protein is thereby obtained.

This von Willebrand Factor thereby constitutes a pharmaceutical composition of very great value, which makes it possible to inject a patient suffering from von Willebrand's disease with only the amounts of product necessary for treating this disease, thereby constituting a decisive technical advance.

In effect, by the invention, the yield of the process per liter of plasma is of the order of 350 international units of von Willebrand factor:RCO and is 600 international units of von Willebrand factor:RAg.

A further point to note is that this product displays very great stability over time. In particular, the activity of the von Willebrand Factor has fallen by less than 5% after 24 hours following the taking up of the lyophilisate.

It should be noted Rag mean Ristocetin antigen.

Further it is clear from the above that by combining the processing steps of examples 1 and 2 selective separation of both Factor VIIIc essentially devoid of von Willebrand, and von Willebrand Factor essentially devoid of Factor VIIIc can be performed. Also it should be noted that the third and sixth conditioning buffer solutions are identical. In addition the gels of the first and second column are identical. This simplifies, improves rationalization and lowers the total cost of the manufacture of Factor VIIIc and von Willebrand Factor. Thus constitutes a remarkable positive result of the invention.

We claim:

1. A process for the manufacture of antihemophilic factor (FVIIIc) having an antihemophilic activity of at least about 250 international units per milligram of proteins, devoid of the major portion of von Willebrand factor, comprising the following steps of:

(a) preparing a first buffered eluting solution having an ionic strength capable of separating factor VIIIc from a major part of the von Willebrand factor and main plasma contaminants, said first buffered eluting solution having a composition of:
NaCl 250 mM,
Tris 20 mM,
$CaCl_2.2H_2O$ 10 mM,
said composition being brought to pH of 6.6;

(b) preparing a crude solution of the factor VIIIc from a cryoprecipitate having a substantially identical ionic strength to that of said first buffered eluting solution;

(c) equilibrating an anionic exchange gel based on crosslinked agarose of a quaternary amine in a first chromatography column with said first buffered eluting solution;

(d) selectively adsorbing the factor VIIIc by passing said crude solution through said anionic exchange gel of said first chromatography column and eluting said crude solution with said first buffered eluting solution, thereby having said factor VIIIc selectively adsorbed on the anionic exchange gel of the first chromatography column, whereas the major portion of the von Willebrand factor is not adsorbed by the anionic exchange gel of the first chromatography column;

(e) desorbing said adsorbed factor VIIIc by eluting said anionic exchange gel of said first chromatography column by using a second buffered eluting solution of ionic strength higher than that of said first buffered eluting solution; and (f) collecting the factor VIIIc desorbed with said second buffered eluting solution, said factor VIIIc being devoid of a major portion of the von Willebrand factor and other main plasma contaminants;

thereby obtaining said antihemophilic factor (FVIIIc) with an antihemophilic activity of at least about 250 international units per milligram of proteins.

2. The process of claim 1, wherein said anionic exchange gel is in the form of agarose beads which have short $C_1$–$C_6$ alkylene spacer-arms that link the quaternary amine to the agarose beads.

3. The process of claim 2, wherein the anionic exchange gel comprises 6% agarose beads and the agarose beads have a diameter of 45 to 165 µm in a wet state.

4. The process of claim 1, wherein the crude solution of factor VIIIc is virally inactivated prior to said selectively adsorbing step.

5. The process of claim 1, wherein diafiltration of the crude solution of factor VIIIc is carried out against the first buffered eluting solution.

6. The process of claim 1, wherein the purified solution of factor VIIIc is concentrated and lyophilized.

7. The process of claim 1, wherein the crude solution to be purified is prepared by dissolving a cryoprecipitate of a human plasma extract.

8. The process of claim 1, wherein the crude solution is obtained by dissolving the cryoprecipitate in water containing heparin thereby having a heparin containing crude solution and said heparin containing crude solution is treated with aluminum hydroxide.

9. The process of claim 8, wherein the proportion in which aluminum hydroxide is incorporated into said crude solution is at least 10% by volume, relative to the total volume of the crude solution containing factor VIIIc.

10. The process of claim 8, wherein centrifugation is carried out in order to separate the aluminum hydroxide from the crude solution of factor VIIIc, from which vitamin K dependent factors are thereby removed.

11. The process of claim 1, wherein the factor VIIIc collected with the second buffered eluting solution is subjected to diafiltration against a third buffer solution.

12. The process of claim 1, wherein the second buffered eluting solution used for desorption of the factor VIIIc from the column, has the following composition:

NaCl 700 mM,
Tris 20 mM,
$CaCl_2.2H_2O$ 10 mM,
this composition being brought to pH 6.6.

13. The process of claim 11, wherein the third buffer solution mentioned above, used for diafiltration of the purified and eluted factor VIIIc, has the following composition:

NaCl 100 mM,
Tris 20 mM,
$CaCl_2.2H_2O$ 0.6 mM,
L-arginine 17 mM,
L-lysine-HCl 20 mM,
this solution being brought to pH 7.

14. The process of claim 11, wherein, before this diafiltration is carried out with the third buffer solution, 17 mM of L-arginine and 20 mM of L-lysine-HCl per liter of solution are added to the factor VIIIc collected with the second buffered eluting solution.

15. The process of claim 1, wherein the factor VIIIc solution obtained after step (f) is subjected to sterilizing filtration on a sterilizing filter with a pore diameter of 0.22 µm, and this purified and sterilized solution of factor VIIIc is then introduced into silicone-treated flasks.

16. The process of claim 11, wherein the diafiltration is performed with a diafiltration membrane treated with a 0.1M bicarbonate buffer at pH 9.6, containing 30 g/l of non-pyrogenic human albumin and 0.1% by volume of emulsifier.

17. A process for the manufacture of purified factor VIIIc and purified von Willebrand factor comprising the steps of:

(a) preparing a first buffered eluting solution having an ionic strength capable of separating factor VIIIc from a major part of the von Willebrand factor and main plasma contaminants, said first buffered eluting solution having a composition of:
NaCl 250 mM,
Tris 20 mM,
$CaCl_2.2H_2O$ 10 mM,
said composition being brought to pH of 6.6;

(b) preparing a crude solution of the factor VIIIc from a cryoprecipitate having a substantially identical ionic strength to that of said first buffered eluting solution;

(c) equilibrating a first anionic exchange gel based on cross-linked agarose of a quaternary amine in a first chromatography column with said first buffered eluting solution;

(d) selectively adsorbing the factor VIIIc on said first anionic exchange gel in said first chromatography column by passing said crude solution through said first anionic exchange gel of said first chromatography column and eluting said crude solution with said first buffered eluting solution, thereby having said factor VIIIc selectively adsorbed on the first anionic exchange gel of the first chromatography column, whereas the major portion of the von Willebrand factor is not adsorbed by said first gel in said first column, and is present in a non-retained fraction which is collected;

(e) desorbing said adsorbed factor VIIIc by eluting said first anionic exchange gel of said first chromatography column by using a second buffered eluting solution of ionic strength higher than that of said first buffered eluting solution; and (f) collecting the factor VIIIc desorbed with said second buffered eluting solution, said factor VIIIc being devoid of a major portion of the von Willebrand factor and other main plasma contaminants;

(g) treating the non-retained fraction containing the von Willebrand factor to decrease the ionic strength of said non-retained fraction until an ionic strength, corresponding to that which is obtained with a 0.10–0.15M NaCl solution is obtained;

(h) adsorbing said non-retained fraction containing the von Willebrand factor with decreased ionic strength on a second ionic exchange gel based on cross-linked agarose of a quaternary amine in a second chromatography column, which has been equilibrated with a third buffered eluting solution having the said decreased ionic strength and containing 0.10–0.15M NaCl, thereby having said von Willebrand factor selectively adsorbed on the second ionic exchange gel of the second chromatography column, whereas the major portion of the contaminant proteins is not adsorbed;

(i) desorbing said adsorbed von Willebrand factor by eluting s aid second ionic exchange gel of said second chromatography column by using a fourth buffered eluting solution of ionic strength higher than that of a third buffered eluting solution;

(j) collecting the von Willebrand factor desorbed with said fourth buffered eluting solution, said von Willebrand factor being devoid of major portion of factor VIIIc and other main plasma contaminants.

18. The process of claim 17, wherein the third buffered eluting solution comprises the following composition:

NaCl 100–150 mM,

Tris 20 mM, pH 6.6.

19. The process of claim 17, wherein the fourth buffered eluting solution for desorbing von Willebrand factor from said second chromatography column comprises the following compositions:

NaCl 350 mM,

Tris 20 mM, pH 6.6.

20. The process of claim 17, wherein the von Willebrarnd factor is concentrated and diafiltrated against a conditioning buffer solution permitting an intravenous injection.

21. The process of claim 17, wherein said first anionic exchange gel and said second ionic exchange gel are identical; said gels being in the form of agarose beads which have $C_1$–$C_6$ alkylene spacer-arms that link the quaternary amine to the agarose beads.

22. The process of claim 21, wherein each of said first and said second gel comprises 6% agarose beads and the agarose beads have a diameter of 45 to 165 micrometers in a wet state.

23. The process of claim 17, wherein said cryoprecipitate is extracted from human plasma and is dissolved in a water solution containing heparin, said solution being then treated with aluminum hydroxide.

24. The process of claim 23, wherein the proportion of aluminum hydroxide is at least 10% by volume relative to the total volume of the solution.

25. The process of claim 17, wherein the crude solution containing factor VIIIc and von Willebrand factor is virally inactivated.

26. The process of claim 17, wherein said von Willebrand factor is obtained in a yield per liter of plasma of about 350 international units of von Willebrand factor: RCO as measured by diafiltration.

* * * * *

UNITED STATES PATENT AND TRADEMARK OFFICE
CERTIFICATE OF CORRECTION

PATENT NO. : 5,760,183

DATED : June 2, 1998

INVENTOR(S) : Bernard Dazey, Mohamed Hamsany and Gérard Vezon

It is certified that an error appears in the above-identified patent and that said Letters Patent is hereby corrected as shown below:

On the title page item [54] should read as follows:

[54] PROCESS FOR THE MANUFACTURE OF VERY HIGH-PURITY ANTIHAEMOPHILIC FACTOR (FVIIIC), AND VON WILLEBRAND FACTOR, AND PHARMACEUTICAL COMPOSITIONS CONTAINING SAME

Signed and Sealed this

Thirteenth Day of October 1998

Attest:

BRUCE LEHMAN

Attesting Officer

Commissioner of Patents and Trademarks